(12) United States Patent
Schmid et al.

(10) Patent No.: US 8,800,553 B2
(45) Date of Patent: Aug. 12, 2014

(54) RESPIRATOR FLOW SENSOR

(75) Inventors: Uwe Schmid, Lübeck (DE); Andreas Brandt, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 177 days.

(21) Appl. No.: 13/045,140

(22) Filed: Mar. 10, 2011

(65) Prior Publication Data

US 2011/0247615 A1 Oct. 13, 2011

(30) Foreign Application Priority Data

Apr. 10, 2010 (DE) .......................... 10 2010 014 873

(51) Int. Cl.
| | |
|---|---|
| *A61M 16/01* | (2006.01) |
| *B29C 65/00* | (2006.01) |
| *B29C 45/00* | (2006.01) |
| *A61M 15/00* | (2006.01) |
| *A61M 16/00* | (2006.01) |

(52) U.S. Cl.
USPC .................................................. 128/203.12

(58) Field of Classification Search
USPC .............. 73/196, 197, 202.5, 861.42, 861.52, 73/861.64; 128/203.12, 204.18, 204.23, 128/200.24; 600/529, 533, 538
See application file for complete search history.

(56) References Cited

U.S. PATENT DOCUMENTS

| | | | |
|---|---|---|---|
| 5,134,890 A | | 8/1992 | Abrams |
| 5,379,650 A | * | 1/1995 | Kofoed et al. ............. 73/861.52 |
| 5,631,417 A | * | 5/1997 | Harrington et al. ........ 73/204.26 |
| 6,119,723 A | | 9/2000 | Kenyon |
| 7,579,823 B1 | * | 8/2009 | Ayliffe ......................... 324/71.1 |
| 8,446,021 B2 | | 5/2013 | Maeurer et al. |
| 2002/0078744 A1 | * | 6/2002 | Gehman et al. ............ 73/204.11 |

FOREIGN PATENT DOCUMENTS

| | | |
|---|---|---|
| CN | 1 548 175 A | 11/2004 |
| WO | 2009/043614 A2 | 4/2009 |

* cited by examiner

*Primary Examiner* — Tan-Uyen T Ho
*Assistant Examiner* — Mark Wardas
(74) *Attorney, Agent, or Firm* — McGlew and Tuttle, P.C.

(57) ABSTRACT

A respirator or anesthesia apparatus for the artificial respiration of a patient is provided with a gas delivery device, at least one gas line for forming a breathing air line system, at least one device for measuring a volume flow of a gas according to the differential pressure method with a flow channel, a first pressure-measuring point and a second pressure-measuring point. The second pressure-measuring point is arranged in the direction of flow of the gas to be measured after the first pressure-measuring point at the flow channel. Furthermore, the flow channel is split into at least two separate partial flow channels in the direction of flow of the gas to be measured between the first pressure-measuring point and the second pressure-measuring point.

10 Claims, 2 Drawing Sheets

RESPIRATOR FLOW SENSOR

CROSS REFERENCE TO RELATED APPLICATIONS

This application claims the benefit of priority under 35 U.S.C. §119 of German Patent Application DE 10 2010 014 873.3 filed Apr. 10, 2010, the entire contents of which are incorporated herein by reference.

FIELD OF THE INVENTION

The present invention pertains to a respirator (also known as a ventilator) and anesthesia apparatus for the artificial respiration (ventilation) of a patient, including a gas delivery means, at least one gas line for forming a breathing air line system, especially a breathing air circulation system and at least one means for measuring a volume flow of a gas according to a differential pressure method and to a process of manufacturing a respirator and anesthesia apparatus.

BACKGROUND OF THE INVENTION

Artificial respiration of patients is necessary for various medical applications, e.g., during surgery. Respirators are used for the artificial respiration of patients and can additionally also be used for anesthesia as anesthesia apparatuses with an anesthetic reflector and anesthetic dispenser. The expiration gas expired by the patient can be reused again at least partly as inspiration gas in some respirators, i.e., these represent a rebreathing system with a breathing air circulation system. A gas delivery means, which ensures that the gas used up by the patient, for example, oxygen, is added again to the inspiration gas, is present in the respirator with the breathing air circulation system.

Measurement of a volume flow of one or more gases is necessary in respirators or anesthesia apparatuses. It is necessary, in particular, in a gas mixer of an anesthesia apparatus, to measure the volume flows of the different gases fed to the gas mixer, for example, oxygen, laughing gas and air. The gas, whose volume flow is to be measured, is sent through a flow channel with a first pressure-measuring point and a second pressure-measuring point. The flow channel has a cross section contraction between the first and second pressure-measuring points. Increased friction, which leads to a loss of energy of the gas, which can be measured as a pressure drop, will develop in the cross section contraction due to the increased velocity. The volume flow can be calculated from the measured pressure difference. Additional parameters, for example, the absolute pressure, temperature and geometric properties of the flow channel as a measuring channel, are necessary here. A U-shaped channel is used as a flow channel in the direction of flow of the gas to be measured. The U-shaped channel comprises three holes arranged at right angles in relation to one another in an aluminum block. As an alternative, a sintered body or a gap may also be used to contract the cross section. The manufacture of the U-shaped channel with the three holes arranged at right angles in relation to one another is complicated by means of injection molding with an injection die because slides are necessary for this. Narrow gaps can also be prepared with difficulty only by means of injection molding as a cross section contraction, e.g., as a diaphragm, because thin die structures, which are highly unstable, are to be prepared for this. Long flow channels are also disadvantageous because of the large space required at a respirator or anesthesia apparatus.

SUMMARY OF THE INVENTION

The object of the present invention is therefore to make available a respirator or anesthesia apparatus and a process for manufacturing a respirator or anesthesia apparatus, in which the volume flow of a gas can be measured with a means according to the differential pressure method and said means can be manufactured in a simple manner at a low cost.

This object is accomplished with a respirator or anesthesia apparatus for the artificial respiration of a patient, comprising a gas delivery means, at least one gas line for forming a breathing air line system, especially a breathing air circulating system, at least one means for measuring a volume flow of a gas according to a differential pressure method with a flow channel, a first pressure-measuring point and a second pressure-measuring point, wherein the second pressure-measuring point is arranged at the flow channel in the direction of flow of the gas to be measured after the first pressure-measuring point. Furthermore, the flow channel is divided into at least two separate partial flow channels in the direction of flow of the gas to be measured between the first pressure-measuring point and the second pressure-measuring point.

Due to the splitting of the gas to be measured between the first and second pressure-measuring points into at least two partial flows, which are sent through the at least two partial flow channels, the means or manufacture is especially simple and inexpensive.

In particular, the at least two separate partial flow channels have a curved flow space in the direction of flow of the gas to be measured.

In another embodiment, the flow space of the at least two separate partial flow channels has essentially a constant curvature in the direction of flow of the gas to be measured. An essentially constant curvature means that the flow space of the at least two separate partial flow channels has a curvature difference of less than 50%, 40%, 30%, 20%, 10% or 5%.

The at least two separate partial flow channels are formed around a cylinder in an additional embodiment.

The flow space with the essentially constant curvature of the at least two separate partial flow channels is preferably directed eccentrically in relation to the cylinder. Due to the eccentric arrangement, fluctuations of the flows between the two partial flow channels can be reduced or eliminated.

Instead of a curved flow space of the partial flow channels in the direction of flow of the gas to be measured, the flow space may also be directed or designed in a U-shaped or L-shaped manner. In case of a curved flow space, this flow space is preferably of a semicircular shape and the flow space may also have a U-shaped design as an alternative instead of the semicircular design of the flow space.

In one variant, the flow space of the at least two separate partial flow channels is directed in an L- or U-shaped manner in the direction of flow of the gas.

The flow channel, especially the at least two separate partial flow channels, are preferably manufactured from a thermoplastic plastic with a bottom part and a cover part. The flow channel, especially the at least two separate partial flow channels, can thus also be manufactured by means of injection molding in an especially simple manner and at a low cost.

In another embodiment, the bottom part forms a bottom and at least one side wall of the at least two separate partial flow channels, and the cover part forms the cover wall of the at least two separate partial flow channels.

In an additional embodiment, the bottom part and the cover part are connected to one another in substance, especially by means of welding, especially a thermoplastic plastic.

In particular, a cross section contraction in the flow channel, especially in the at least two separate partial flow channels, is formed between the first and second pressure-measuring points in the direction of flow of the gas.

In an additional embodiment, the diameter of the at least two partial flow channels is between 0.5 mm and 8 mm and especially between 0.5 mm and 3 mm.

In an additional variant, the flow channel has and/or the at least two partial flow channels have a rectangular, square, triangular or round cross section.

In an additional variant, the volume flow of the gases to be fed to the gas mixture can be measured by the at least one means for measuring the volume flow of the gas.

A process according to the present invention for manufacturing a respirator or anesthesia apparatus, especially a respirator or anesthesia apparatus described herein, includes the steps of making available a gas delivery means, of making available at least one gas line to form a breathing air line system, especially a breathing air circulation system, of manufacturing at least one means for measuring a volume flow of a gas according to the differential pressure method with a flow channel, with a first pressure-measuring point r and with a second pressure-measuring point, wherein the second pressure-measuring point is arranged in the direction of flow of the gas to be measured after the first pressure-measuring point at the flow channel, wherein the flow channel, especially at least two separate partial flow channels, are manufactured at least partly and especially completely by injection molding between the first and second pressure-measuring points in the direction of flow of the gas. The flow channel, especially the at least two separate partial flow channels, thus represent a measuring section for detecting the volume flow and preferably have a cross section contraction between the first and second pressure-measuring points.

In an additional variant, the flow channel is manufactured from a preferably thermoplastic plastic.

A bottom part and a cover part are manufactured separately by injection molding in another variant and the cover part is subsequently attached to the bottom part, especially in substance, e.g., by welding, so that the flow channel is formed between the bottom part and the cover part.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
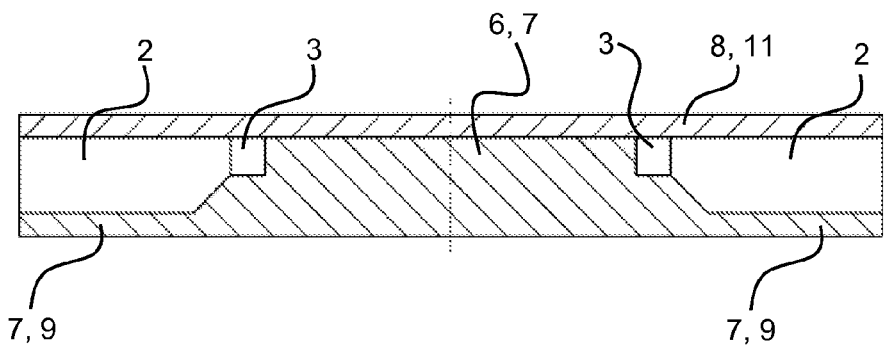
FIG. 2 is a sectional view taken along line A-A of the means according to FIG. 1.
Figure 3:
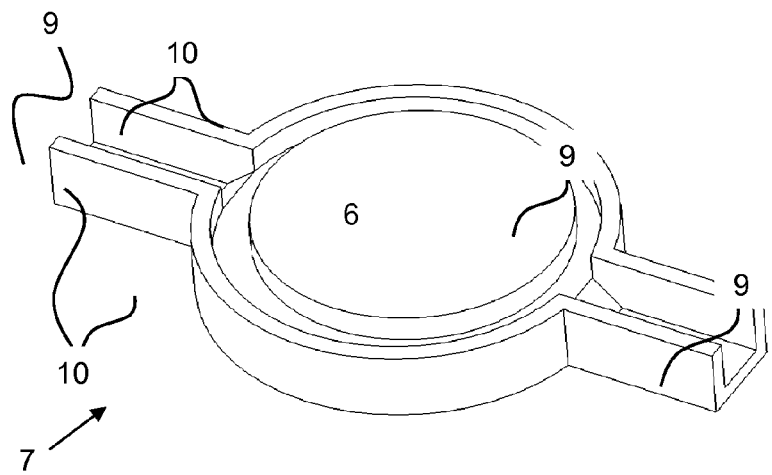
FIG. 3 is a perspective view of a bottom part of the means according to FIG. 1.
Figure 4:
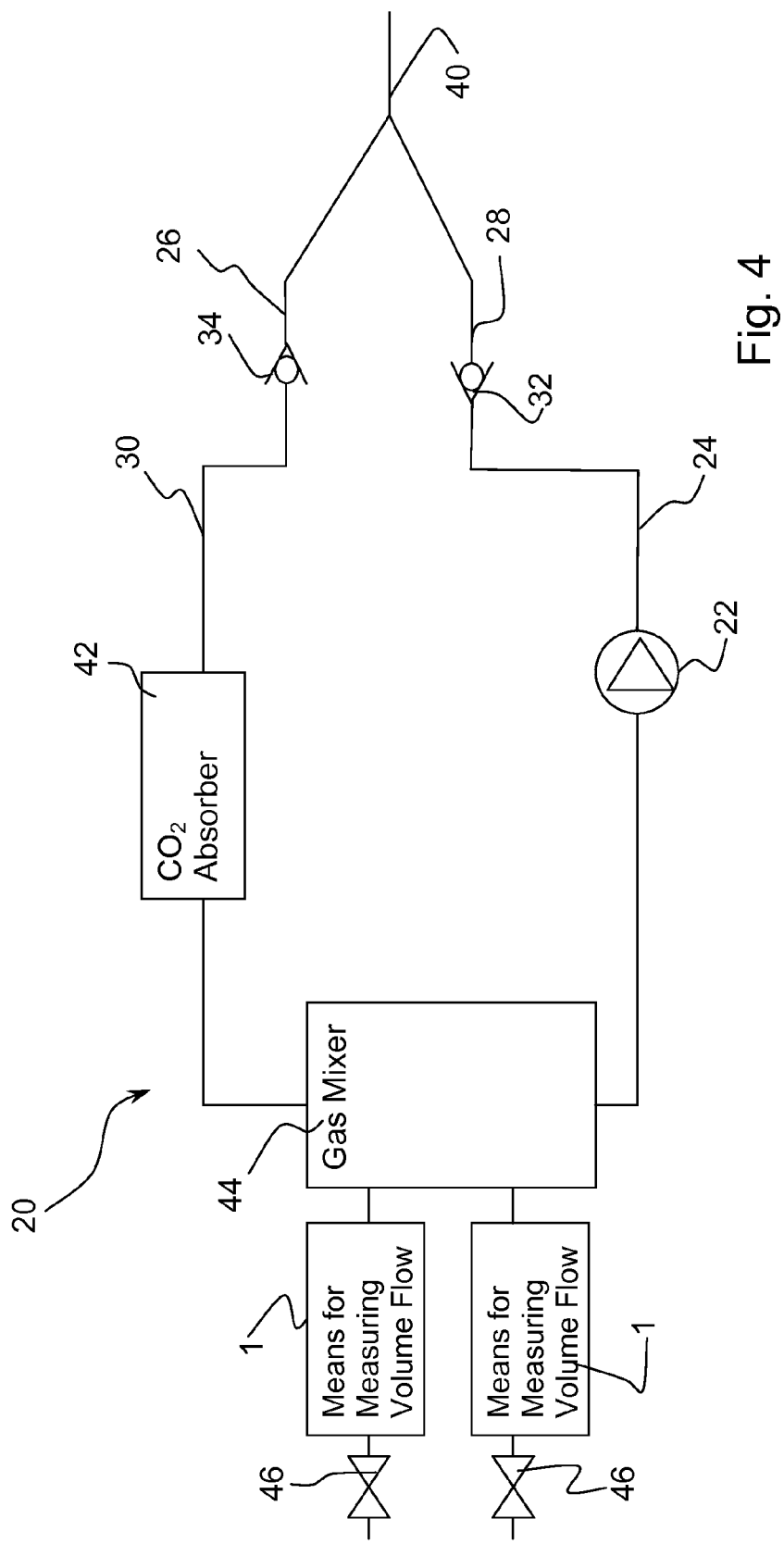
FIG. 4 is a schematic view of a respirator or anesthesia apparatus.

Referring to the drawings in particular, a means for measuring the volume flow of a gas 1 is provided as part of a respirator 20. Such respirators are used for the artificial respiration of patients and anesthesia apparatuses are used, besides for respiration, also for the anesthesia of patients. FIG. 4 shows a respirator or anesthesia apparatus 20 having a breathing air circulation system, i.e., the expiration gas expired by the patient is reused for rebreathing as an inspiration gas. The breathing air is sent by a gas delivery means 22 through gas lines 24 in a breathing air circulation system 30. A first, inspiratory nonreturn valve 32 and a second, expiratory nonreturn valve 34 are arranged in the gas lines. An expiration gas line and an expiration gas tube 26 and an inspiration gas line and an inspiration gas tube 28 are formed as a result. A Y-piece 40, which sends the inspiration gas and the expiration gas to and from a patient to be respirated artificially, is connected to the end of the inspiration gas line 28 and the expiration gas line 26. A $CO_2$ absorber 42 absorbs the carbon dioxide contained in the expiration gas. Furthermore, the inspiration gas is enriched with anesthetic with an anesthetic reflector and an anesthetic (not shown). In addition, a mixture of oxygen and laughing gas is fed to the inspiration gas by means of a gas mixer 44. Oxygen and laughing gas are fed separately to the gas mixer by means of two valves 46. The volume flow of the oxygen and laughing gas to be fed to the gas mixer is now to be detected by means of a means for measuring the volume flow 1 of a gas, namely, the oxygen and laughing gas (FIGS. 1 through 3).

Means 1 has a bottom part 7 and a cover part 8. The bottom part 7 and cover part 8 are manufactured by injection molding from a thermoplastic plastic and are connected to one another after the injection molding in substance, i.e., by means of welding the thermoplastic plastic. Bottom part 7 has a bottom 9, side walls 10 and a cylinder 6. Cover part 8 forms a cover wall 11 of means 1. A flow channel 2 is defined here by the bottom 9, two side walls 10 and the cover wall 11. A first pressure-measuring point (sensor) 4 and a second pressure-measuring point (sensor) 5 are arranged at the flow channel 2 (FIG. 1). Two partial flow channels 3 are present in the direction of flow of the gas to be measured with means 5 between the first pressure-measuring point 4 and the second pressure-measuring point 5, which are each arranged at the flow channel 2. Flow channel 2 opens into the two partial flow channels 3 and the two partial flow channels 3 open into flow channel 2. The two partial flow channels 3 are defined downwardly by the bottom 9, laterally by a side wall 10 and the cylinder 6 and upwardly by the cover wall 11. The flow space of the two partial flow channels 3 is provided with a constant curvature in the direction of flow of the gas to be measured, namely, oxygen and laughing gas, and it is essentially a semicircle. The upper partial flow channel 3 shown in FIG. 1 thus represents an upper semicircle and the lower partial flow channel 3 shown in FIG. 1 represents a lower semicircle.

A hydraulic diameter of the two partial flow channels 3 is smaller than a hydraulic diameter of flow channel 2 at the first and second pressure-measuring points 4, 5. Thus, there is a cross section contraction between the first and second pressure-measuring points 4, 5 and the volume flow of the gas can be detected and calculated by means of the pressure difference detected by the first and second pressure-measuring points 4, 5. The anesthesia apparatus has at least one means 1. A pressure difference of 0 mbar to 200 mbar will become established between the first and second pressure-measuring points 4, 5 at a volume flow between 0 L per minute and 80 L per minute.

Figure 1:
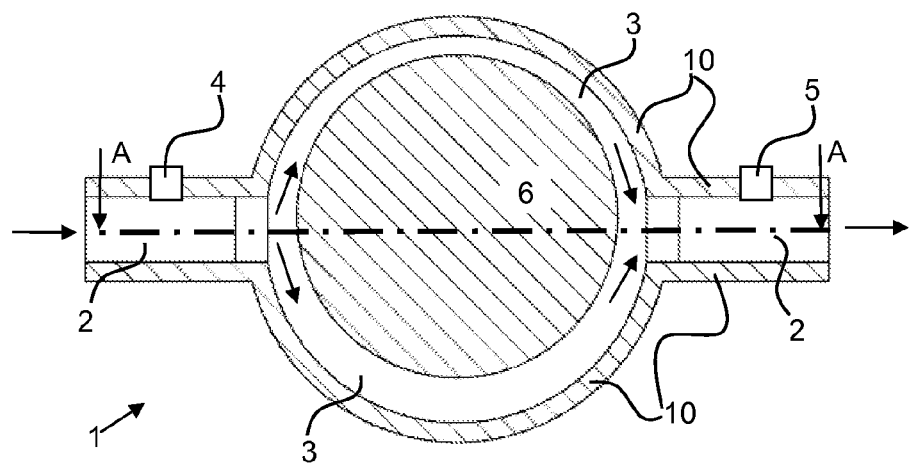
FIG. 1 is a sectional view of a means for measuring a volume flow of a gas according to the differential pressure method.

Cylinder 6 is directed eccentrically in relation to the side walls 10 at the two partial flow channels 3, so that the upper partial flow channel 3 in FIG. 1 has a smaller cross-sectional area than the lower partial flow channel 3 shown in FIG. 1.

Cyclic fluctuations in the flows between the two partial flow channels 3 can be avoided as a result. Means 1 can be manufactured in a very simple manner by means of injection molding from a thermoplastic plastic with an injection die. Bottom part 7 is manufactured with an injection die, and cover part 8 is manufactured with another injection die. Thus, only two components, namely, bottom part 7 and cover part 8, are to be manufactured by injection molding. Only the cover part 8 needs subsequently to be placed on the bottom part 7 and hot-welded to same, so that the means 1 can thus be manufactured in a simple manner. Only the two pressure-measuring points 4, 5 are still to be arranged in the direction of flow of the gas to be measured before and after the two partial flow channels 3. Furthermore, means 1 may be integrated in the gas mixer 44.

On the whole, essential advantages are associated with the respirator or anesthesia apparatus according to the present invention. Means 1 for measuring a volume flow of a gas can be manufactured with a simple design by means of injection molding from a thermoplastic plastic. The costs for manufacturing the means 1 can thus be substantially reduced.

While specific embodiments of the invention have been described in detail to illustrate the application of the principles of the invention, it will be understood that the invention may be embodied otherwise without departing from such principles.

APPENDIX

LIST OF REFERENCE NUMBERS

| | |
|---|---|
| 1 | Device for measuring a volume flow |
| 2 | Flow channel |
| 3 | Partial flow channel |
| 4 | First pressure-measuring point |
| 5 | Second pressure-measuring point |
| 6 | Cylinder |
| 7 | Bottom part |
| 8 | Cover part |
| 9 | Bottom |
| 10 | Side wall |
| 11 | Cover wall |
| 20 | respirator or anesthesia apparatus |
| 22 | gas delivery means |
| 24 | gas lines |
| 26 | expiration gas line and an expiration gas tube |
| 28 | inspiration gas line and an inspiration gas tube |
| 30 | breathing air circulation system |
| 32 | inspiratory nonreturn valve |
| 34 | expiratory nonreturn valve |
| 40 | Y-piece |
| 42 | $CO_2$ absorber |
| 44 | gas mixer |
| 46. | valves |

What is claimed is:

1. A respirator or anesthesia apparatus for the artificial respiration of a patient, the apparatus comprising:
   a gas delivery device;
   at least one gas line for forming a breathing air line system; and
   a volume flow measuring device for gas volume flow measurement according to sensed differential pressure, the volume flow measuring device including a flow channel, a first pressure-measuring point and a second pressure-measuring point, wherein the second pressure-measuring point is arranged in the direction of flow of the gas to be measured after the first pressure-measuring point at the flow channel, the flow channel being divided into at least two separate partial flow channels in the direction of flow of the gas to be measured between the first pressure-measuring point and the second pressure-measuring point, wherein the flow channel is manufactured from a thermoplastic with a separate bottom part and with a separate cover part, which separate bottom part and separate cover part are joined together at joining surfaces of the separate bottom part and the separate cover part by a connection in substance, wherein, the at least two separate partial flow channels comprise a first curved flow channel, with inner walls and outer walls curved in the direction of flow of the gas to be measured and a second curved flow channel, with inner and outer walls curved in the direction of flow of the gas to be measured, wherein the at least two separate partial flow channels are formed around a common cylinder that has a curvature defined by the inner walls and wherein the outer walls traverse an essentially constant curvature directed eccentrically in relation to the curvature of the common cylinder.

2. A respirator or anesthesia apparatus in accordance with claim 1, wherein each inner wall and each outer wall has an essentially constant curvature in the direction of flow of the gas to be measured essentially constant curvature in the direction of flow of the gas to be measured.

3. A respirator or anesthesia apparatus in accordance with claim 1, wherein the at least two separate partial flow channels are formed around a common cylinder, that is integral with one of the separate bottom part and the separate cover part, and that defines each of the inner walls.

4. A respirator or anesthesia apparatus in accordance with claim 1, wherein the bottom part forms a bottom and at least one side wall of the at least two separate partial flow channels and the cover part forms a cover wall of the at least two separate partial flow channels.

5. A respirator or anesthesia apparatus in accordance with claim 1, wherein the first curved flow channel and the second curved flow channel together have a combined flow cross section that is smaller than a flow cross section of the flow channel upstream of and downstream of the first curved flow channel and the second curved flow channel to provide a cross section contraction that is formed in the flow channel, in the direction of flow of the gas between the first and second pressure-measuring points.

6. A respirator or anesthesia apparatus in accordance with claim 1, wherein a cross section contraction is formed in the two separate partial flow channels, in the direction of flow of the gas between the first and second pressure-measuring points.

7. A respirator or anesthesia apparatus in accordance with claim 1, wherein:
   the bottom part forms a bottom of the two separate partial flow channels;
   the cover part forms a cover wall of the two separate partial flow channels; and
   at least one of the bottom part and the cover part form inner and outer walls as side walls of the two separate partial flow channels.

8. A respirator or anesthesia apparatus in accordance with claim 1, further comprising:
   a first pressure sensor at the first pressure-measuring point; and
   a second pressure sensor at the second pressure-measuring point.

9. A process for manufacturing a respirator or anesthesia apparatus, the process comprising the steps of:
   providing a gas delivery device;
   providing at least one gas line for forming a breathing air line system;

providing a volume flow measuring device for gas volume flow measurement according to sensed differential pressure, the volume flow measuring device including a flow channel, a first pressure-measuring point and a second pressure-measuring point, wherein the second pressure-measuring point is arranged in the direction of flow of the gas to be measured after the first pressure-measuring point at the flow channel; and forming the flow channel so as to be divided into at least two separate partial flow channels in the direction of flow of the gas to be measured between the first pressure-measuring point and the second pressure-measuring point, wherein the two separate partial flow channels, between the first pressure-measuring point and the second pressure-measuring point, are manufactured by injection molding from a thermoplastic material to form a bottom part and a cover part manufactured separately by injection molding, wherein each of the bottom part and the cover part have a joining surface and the cover part joining surface is fastened to the bottom part joining surface so that the two separate partial flow channels are formed between the bottom part and the cover part, wherein the cover part joining surface is fastened to the bottom part joining surface by welding or other thermoplastic material connection in substance along a joining interface, wherein:

the two separate partial flow channels comprise a first curved flow channel, with inner and outer walls curved in the direction of flow of the gas to be measured and a second curved flow channel, with inner and outer walls curved in the direction of flow of the gas to be measured and the first curved flow channel has a smaller cross-sectional area than the second curved flow channel;

the bottom part forms a bottom of the two separate partial flow channels;

the cover part forms a cover wall of the two separate partial flow channels;

a cylinder of one of the bottom part and a cover part defines each of the inner walls; and one of the bottom part and a cover part defines each outer wall, with the outer walls having an essentially constant curvature directed eccentrically in relation to the cylinder.

10. A respirator or anesthesia apparatus for the artificial respiration of a patient, the apparatus comprising:

at least one gas line for forming a breathing air line system with a patient inspiration gas line;

a gas delivery device for delivery of gas through the least one gas line;

a gas feed for feeding gas into the breathing air line system;

a volume flow measuring device for gas volume flow measurement in the gas feed line according to sensed differential pressure, the volume flow measuring device comprises a plastic body defining a flow channel, a first pressure-measuring point and a second pressure-measuring point, wherein the second pressure-measuring point is arranged in the direction of flow of the gas to be measured after the first pressure-measuring point at the flow channel, the flow channel being divided into at least two separate partial flow channels in the direction of flow of the gas to be measured between the first pressure-measuring point and the second pressure-measuring point, wherein the at least two separate partial flow channels each have a curved flow space, curved in the direction of flow of the gas to be measured, wherein the two separate partial flow channels comprise a first curved flow channel, with the inner and outer walls curved in the direction of flow of the gas to be measured and a second curved flow channel, with inner and outer walls curved in the direction of flow of the gas to be measured, wherein the first curved flow channel has a smaller cross-sectional area than the second curved flow channel and the plastic body comprises a bottom part and a cover part and a thermoplastic material connection in substance joining the bottom part and the cover part so that the two separate partial flow channels are formed between the bottom part and the cover part, wherein:

the plastic body is manufactured from a thermoplastic with the bottom part and with the cover part manufactured separately by injection molding;

each of the bottom part and the cover part have a joining surface and the cover part joining surface is fastened to the bottom part joining surface along a joining interface;

the cover part joining surface is fastened to the bottom part joining surface by welding or other connection in substance, along the joining interface, providing the thermoplastic material connection in substance joining the separate bottom part and a separate cover part;

the bottom part forms a bottom of the two separate partial flow channels;

the cover part forms a top wall of the two separate partial flow channels;

one of the bottom part and the cover part form the outer walls;

a circular cylinder of one of the bottom part and a cover part defines the inner walls; and each outer wall has an essentially constant curvature with a center of curvature that is eccentric in relation to a center of curvature of the circular cylinder and is defined by the one of the bottom part and a cover part.

* * * * *